(12) United States Patent
Schmidt et al.

(10) Patent No.: US 11,047,372 B2
(45) Date of Patent: Jun. 29, 2021

(54) EVAPORATOR UNIT FOR AN INHALER

(71) Applicant: HAUNI MASCHINENBAU GMBH, Hamburg (DE)

(72) Inventors: Rene Schmidt, Buchholz i.d.N. (DE); Marc Kessler, Hamburg (DE)

(73) Assignee: HAUNI MASCHINENBAU GMBH, Hamburg (DE)

( * ) Notice: Subject to any disclaimer, the term of this patent is extended or adjusted under 35 U.S.C. 154(b) by 620 days.

(21) Appl. No.: 15/913,454

(22) Filed: Mar. 6, 2018

(65) Prior Publication Data
US 2018/0249763 A1 Sep. 6, 2018

(30) Foreign Application Priority Data

Mar. 6, 2017 (DE) .................. 10 2017 104 555.4

(51) Int. Cl.
A24F 47/00 (2020.01)
F04B 17/03 (2006.01)
F04B 23/04 (2006.01)
F04B 19/00 (2006.01)
F04B 43/04 (2006.01)
A61M 11/04 (2006.01)
A61M 15/06 (2006.01)

(52) U.S. Cl.
CPC ............ *F04B 17/03* (2013.01); *A24F 47/008* (2013.01); *A61M 11/042* (2014.02); *A61M 15/06* (2013.01); *F04B 19/006* (2013.01); *F04B 23/04* (2013.01); *F04B 43/043* (2013.01)

(58) Field of Classification Search
None
See application file for complete search history.

(56) References Cited

U.S. PATENT DOCUMENTS 6,601,776 B1 *  8/2003  Oljaca et al. ............ B05B 1/24
                                                    239/128
2011/0303761 A1  12/2011  Kohnle et al.
2014/0352689 A1  12/2014  Seshadri et al.

FOREIGN PATENT DOCUMENTS

| DE | 2020141101126 | * | 6/2014 |
| DE | 20 2014 101 126 | | 12/2014 |
| EP | 0 539 674 A1 | | 5/1993 |
| EP | 2 397 177 A2 | | 12/2011 |
| WO | WO 01/21319 A1 | | 3/2001 |
| WO | WO 2012/114230 A1 | | 8/2012 |

OTHER PUBLICATIONS

Jeremy A. Walraven, "Introduction to Microelectromechanical Systems (MEMS) Materials, Fabrication Processes and Failure Analysis", pp. 3-5 (59 pages printed form the Internet) (Year: 2012).*
European Search Report issued by the European Patent Office for Application No. 18 159 768.3 dated Jul. 25, 2018, pp. 1-7.

* cited by examiner

*Primary Examiner* — Michael H. Wilson
*Assistant Examiner* — Dionne W. Mayes
(74) *Attorney, Agent, or Firm* — Saliwanchik, Lloyd & Eisenschenk

(57) ABSTRACT

Evaporator unit for an inhaler comprising an evaporator having a heating element for vaporizing a liquid fed through said evaporator. Said evaporator unit comprises a circulation line in which said evaporator is arranged. A circulation device is arranged in said circulation line for circulating the liquid through said circulation line.

16 Claims, 3 Drawing Sheets

EVAPORATOR UNIT FOR AN INHALER

CROSS REFERENCE TO A RELATED APPLICATION

This application claims priority under 35 U.S.C. § 119(e) of German Patent Application No. DE 10 2017 104555.4, filed Mar. 6, 2017, which is incorporated herein by reference in its entirety.

FIELD OF INVENTION

The present invention relates to an evaporator unit for an inhaler, with an evaporator having a heating element for vaporizing a liquid fed through the evaporator.

BACKGROUND OF INVENTION

During vaporizing of e-liquids in usual wick-coil-evaporators with a feeding stream of fresh liquid from the tank, inside the wick a glycerine enriched composition is settled, in which the gas phase composition coincides with that of the feeding stream liquid. This relates to a corresponding boiling temperature. In the wick, a glycerine enriched composition is settled at the edge, which is most likely not constant along the wick. It can be shown, that in this case, in partial areas of the wick higher boiling temperatures have to appear, as if the liquid would have a constant composition during vapor formation, i.e. if the liquid would be well mixed. Furthermore, a composition gradient in the wick profile can lead to hardly controllable spontaneous vaporization of liquid in the centre of the wick, leading to entraining of liquid drops. In terms of a preferably uniform evaporation at a preferably low temperature, this means thermal decomposition of the liquid is avoided, this state should be avoided.

BRIEF SUMMARY

The object of the invention is to provide an evaporator unit in which the liquid in the area of vapor formation, in particular, has a preferably homogeneous composition.

The invention solves this object with the features of the independent claims. According to the invention, the evaporator unit has a circulation line in which the evaporator is arranged. A circulation device is arranged in the circulation line for circulating the liquid through the circulation line. During circulation of the liquid according to the invention, a permanent mixing of the liquid to be vaporized is attained, keeping the composition of the circulated liquid substantially constant. By arranging the evaporator in the circulation line according the invention, a constant liquid composition is realized up to the area of vapor formation, and the primary goal of a constant vapor composition is also attained. Particularly to avoid big local composition gradients, forced convection of the liquid volume enclosed in the circulation line is realized according to the invention.

The circulation device is preferably driven electrically, because an electric energy storage for operating the heating element in the evaporator is provided anyway. The circulation device may in particular be an (electrically driven) pump, preferably a micro pump.

To keep the function of the evaporator unit running, vaporized liquid has to be fed from the liquid storage to the evaporator. For feeding vaporized liquid, favourably a capillary feed, a feed pump, a pressurization device or another suitable feeding mechanism is provided.

The liquid storage is favourably arranged in the circulation line so that the liquid that is stored in the liquid storage is also circulated. This can significantly contribute to reach the goal of a preferably constant liquid composition. But arranging the liquid storage in the circulation line is not absolutely necessary. In other embodiments, the liquid storage is arranged separated from the circulation line. The evaporator unit then preferably has a branching element for supplying liquid from the liquid storage to the circulation line. The branching element is preferably realized as a line, more preferred as a static mixer, and can for example be a labyrinth mixer.

To avoid high thermal loads and corresponding poor responsiveness, the evaporator unit is realized as small as possible. The evaporator and/or evaporator unit are preferably made on the basis of MEMS-technology and therefore preferably as a single microelectromechanical system.

BRIEF DESCRIPTION OF THE DRAWINGS

In the following, the invention is described based on preferred embodiments with reference to the attached figures, which show in FIG. 1 a profile of an electronic cigarette product in one embodiment of the invention.

DETAILED DESCRIPTION

Figure 1:
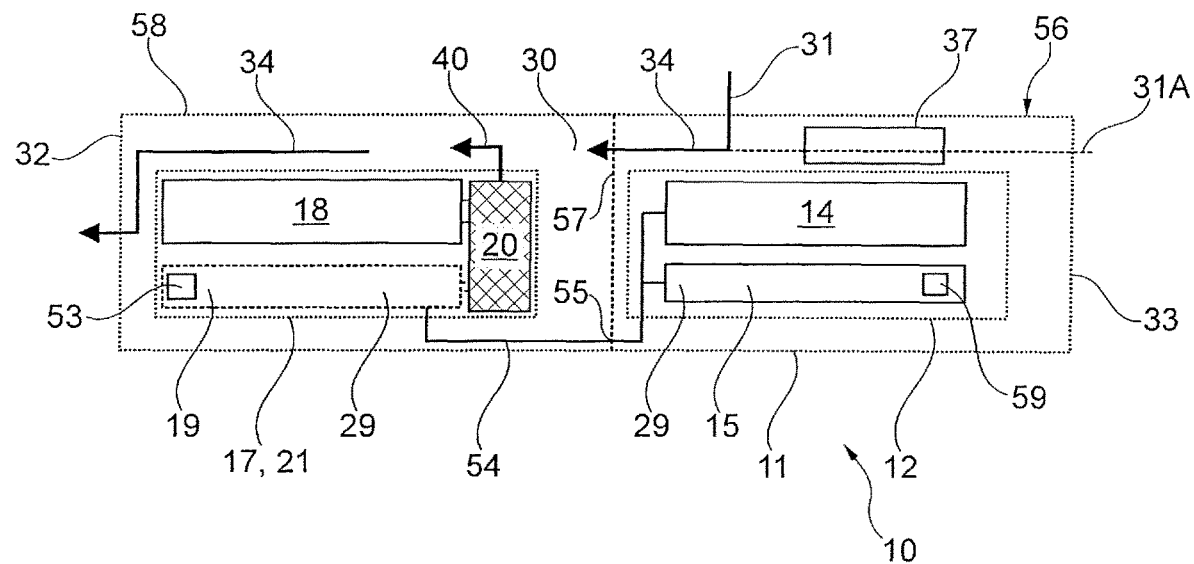

The electronic cigarette product 10 comprises a substantially rod-shaped or cylindrical housing 11. In the housing 11, an air channel 30 is provided between at least one air inlet opening 31 and the mouthpiece 32 of the cigarette product 10. The mouthpiece 32 of the cigarette product 10 is related to the end at which the consumer inhales, thereby applying vacuum to the cigarette product 10 and creating an air stream 34 in the air channel 30. At least one air inlet opening 31 can be arranged at the shell side of the housing 11. Additionally or alternatively, at least one air inlet opening 31A can be arranged at the distant end 33 of the cigarette product 10. The distant end 33 of the cigarette product 10 is referred to the end of the cigarette product 10 opposite to the mouthpiece 32.

Behind one or more air inlets 31, 31A in the flow path of the air stream 34, preferably an air heating device 37 can be arranged for heating up or pre-heating the entering air. Aerosol forming can therefore be optimized. The air heating device 37 can, for example, be arranged adjacently to the power supply unit 14 and/or extend in circumferential direction along the inner shell side of the housing 11.

The air sucked through the inlet opening 31 is transported in the air channel 30 to an evaporator 20 optionally via an interface or parting surface 57. The evaporator 20 adds liquid 50 from the liquid storage 18 as a feed 40 in the form of small liquid drops in a nebula/aerosol and/or gaseous vapor to the air stream 34. A preferable volume of the liquid storage 18 is within the range between 0.1 ml and 5 ml, preferred between 0.5 ml and 3 ml, more preferred between 0.7 ml and 2 ml or 1.5 ml.

The cigarette product 10 comprises, preferably at the distant end 33 of the cigarette product 10, an electronic power supply unit 12 with an electric energy storage 14 and an electric/electronic control device 15. The energy storage 14 can particularly be an electrochemical one-way battery or a rechargeable electrochemical accumulator, for example a lithium ion accumulator. The cigarette product 10 further comprises, preferably at the mouthpiece 32 of the cigarette product 10, an evaporator unit 17 with a liquid storage 18, an electric control device 19 and the evaporator 20.

Instead of the separate electric/electronic control device 15, 19, a single electric/electronic control device can be provided, which can either be arranged in the power supply unit 12 or in the evaporator unit 17. The total of electric/electronic control devices of the cigarette product 10 is in the following referred to as control arrangement 29.

In the housing 11, preferably a sensor is arranged, for example a pressure sensor or a pressure- and flow-switch, wherein the control arrangement determines an operating state of the cigarette product 10, in which a consumer inhales at the mouthpiece 32 of the cigarette product 10, on the basis of a sensor signal output from said sensor. In this operating state, the control arrangement 29 controls the evaporator 20 in order to add liquid from the liquid storage 18 as a feed 40 in the form of small liquid drops in a nebula/aerosol and/or gaseous vapor to the air stream 34.

The liquid in the liquid storage 18, that has to be dispensed (i.e. the liquid component mixture) may for example be a mixture of 1,2-propylene glycol, glycerine and/or water to which one or more flavours and/or agents, for example nicotine, can be added.

The evaporator unit 17 is preferably realized as a cartridge 21 that is exchangeable by the consumer, that means it is realized as a one-way part. The rest of the cigarette product 10, which especially contains the energy storage 14, is preferably realized as a base part 56, which is reusable by the consumer, that means it is realized as a multiple use part. The cartridge 21 is connectable to the base part 56 by the consumer and is realized detachable from the base part 56. Therefore, a parting surface or interface 57 is realized between the cartridge 21 and the reusable base part 56. The cartridge housing 58 may represent a part of the housing 11 of the cigarette product 10.

Figure 2:
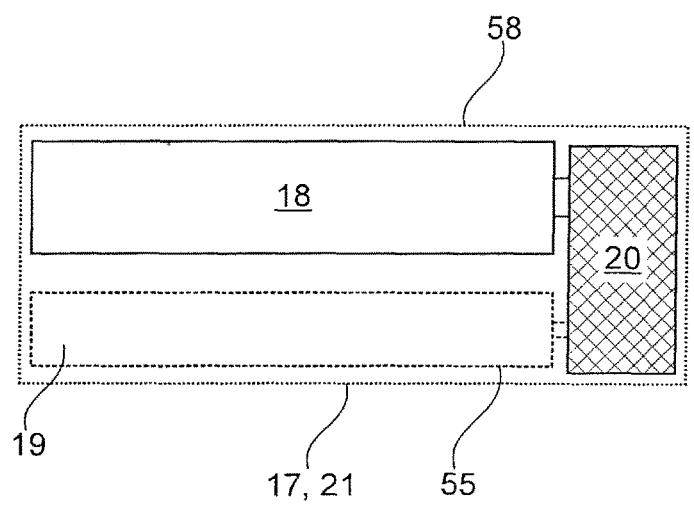
FIG. 2 a profile of a cartridge for an electronic cigarette product.

In other embodiments, see FIG. 2, the evaporator unit 17 is realized as a cartridge 21 which is connectable to the reusable base part 56 of the cigarette product 10 by the consumer and detachable from it. In this case, the cartridge housing 58 is separated from the housing 11 of the cigarette product 10.

The cartridge 21 comprises at least one liquid storage 18. The cartridge 21 can, as shown in FIG. 2, comprise the electric/electronic control device 19. In other embodiments, the electric/electronic control device 19 is a totally or partially fixed component of the base part 56. Likewise, the evaporator 20 can be part of the cartridge 21 or can be arranged in the base part 56. Therefore, in some embodiments the cartridge 21 may essentially only consist of the liquid storage 18 and optionally the cartridge housing 58, said cartridge housing 58 may be alternatively realized by the housing of the liquid storage 18, therefore, a separate cartridge housing 58 may be expendable.

Besides usage in rod-shaped cigarette products 10, the evaporator unit 17 may also be used in other kinds of inhalers, for example in electrical pipes, in shishas, in heat-not-burn products or in a medical inhaler. The energy storage 14 is usually not part of the cartridge 21 but part of the reusable base part 56.

The evaporator unit 17 or the cartridge 21 preferably comprises a non-volatile information storage 53 (see FIG. 1) for storing information or parameters relating to the evaporator unit 17 or the cartridge 21, for example realized as EEPROM, RFID or other suitable kind. The information storage 53 may be realized as a part of the electric/electronic control device 19 or separated from it. In the information storage 53, information is stored preferably related to ingredients, i.e. the composition of the liquid in the liquid storage 18; information about the process profile, especially power-/temperature-control; data for condition monitoring or system check, for example leakage test; data regarding copyright and forgery protection, especially comprising an ID for unique labelling of the evaporator unit 17 or the cartridge 21; serial number, production date and/or expiration date; and/or puff count (number of inhalations by the consumer) or usage time. The data storage 53 is preferably connected or connectable to the control device 19 of the base part 56 via contacts and/or wires.

Preferable embodiments of evaporator units 17 according to the invention are shown in FIGS. 3 to 7.

The evaporator 20 comprises an electric heating element 22 in particular a resistance heating element for heating and therefore vaporizing liquid contacting the heating element 22. The heating element is flown by electric current produced by the energy storage 14 and is therefore heated. The heating current, and therefore the temporal profile of the heating process, is preferably controlled by the electronic control arrangement 29. In the embodiment according to FIGS. 3, 6 and 7, the heating element 22 may for example be a spiral heating element made from a resistance wire. The construction of the heating elements 22 in FIGS. 4 and 5 is described further below.

The evaporator unit 17 comprises the cycle line or circulation line 13 according to the invention, in which the evaporator 20 and an electrically driven circulation device 16 are arranged. The circulation device 16, controlled by the control device 19 or the control arrangement 29, is in particular realized as an electric (circulating-) pump, preferably realized as a micropump. As apparent from FIGS. 3 to 7, the circulation line 13 is a closed cycle, so that if the circulation device 16 is running, the liquid in the circulation line 13 is continuously circulated, establishing an optimal mixing of the liquid and therefore a constant mixing ratio.

Therefore, a forced convection of the liquid volume located in the circulation line 13 is established which passes the liquid by the evaporator 20 and the heating element 22 vaporizing a part of the liquid by thermal influence forming a vapor/aerosol 40. This forced convection is produced by the circulation device 16 and shows such a massive volume flow that vaporization-caused changes of the concentration of the liquid passing the heating element 22 remain at low level.

Figure 3:
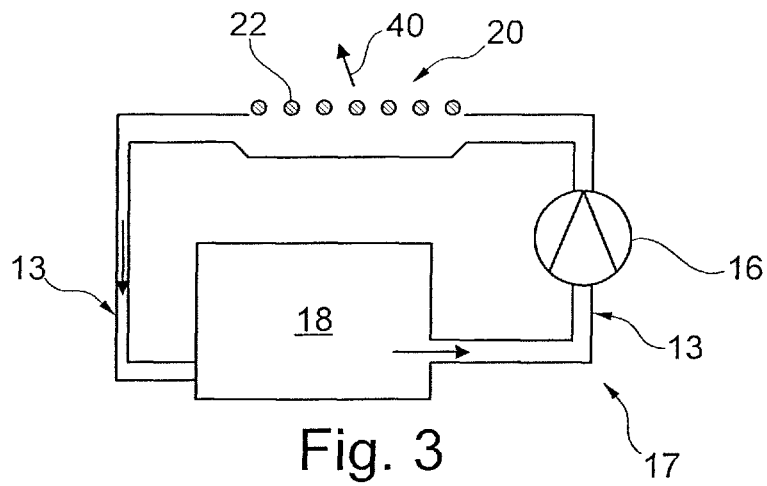
FIGS. 3-7 a schematic view of an evaporator unit in different embodiments of the invention.
Figure 4:
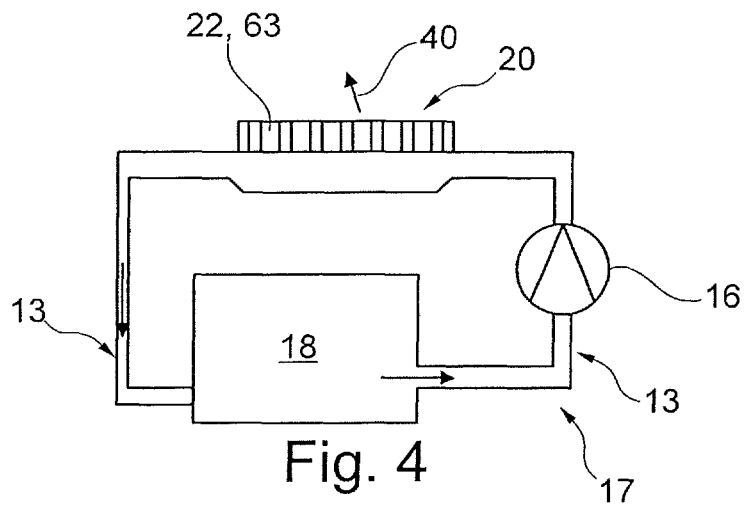
Figure 5:
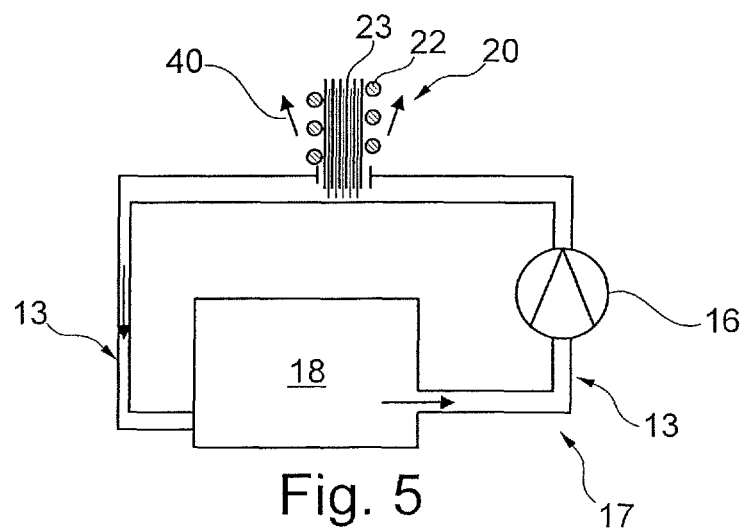

In the preferred embodiments according to FIGS. 3 to 5, the liquid storage 18 is arranged in the circulation line 13 or switched into it, so the total liquid located in the evaporator unit, including the content of the reservoir 18, is circulated by the pump 16 and passed by the heating element 22.

In the embodiments according to FIGS. 3 to 5 and 7, the feeding of the vaporized mass flow 40 is ensured in a suitable manner. This may be done for example by a capillary feeding effect. Therefore, the evaporator 20 according to the embodiment shown in FIG. 4 comprises a block-shaped substrate 63 made from an electrically conducting material which is equipped with a plurality of microchannels which are fluently connecting an inlet side of the substrate 63 with an outlet side. The inlet side is fluently connected with the circulation line 13 and therefore with the liquid storage 18. Due to the dimensions of the microchannels, a capillary effect is preferably established, therefore a liquid entering into a microchannel at the inlet side rises upwards through the microchannel, until the microchannel is filled with liquid. Thus, an automatic capillary feeding effect to compensate vaporized liquid is realized.

An electrical voltage Uh is applied to the substrate 63 by the control device 19 via electrodes resulting in an electrical current flowing through the substrate 63. Due to the ohmic resistance of the substrate 63, the current flow results in a heating of the substrate 63 and thus in vaporization of liquid located in the microchannels. Therefore, the liquid located in the microchannels 62 is driven out of the microchannels 62 in the form of a vapor and/or aerosol 40 due to spontaneous heating. The vapor and/or aerosol produced in this way leaks from the microchannels to the outlet side and is mixed as a vapor feed to the air stream 34, which is passing by the outside of the outlet openings of the substrate 63, as can be seen in FIG. 1.

The embodiment according to FIG. 5 realizes a capillary effect by a wick-coil-evaporator 20, i.e. by a heating coil representing a heating element 22 and a wick 23 arranged in the heating coil 22.

Figure 6:
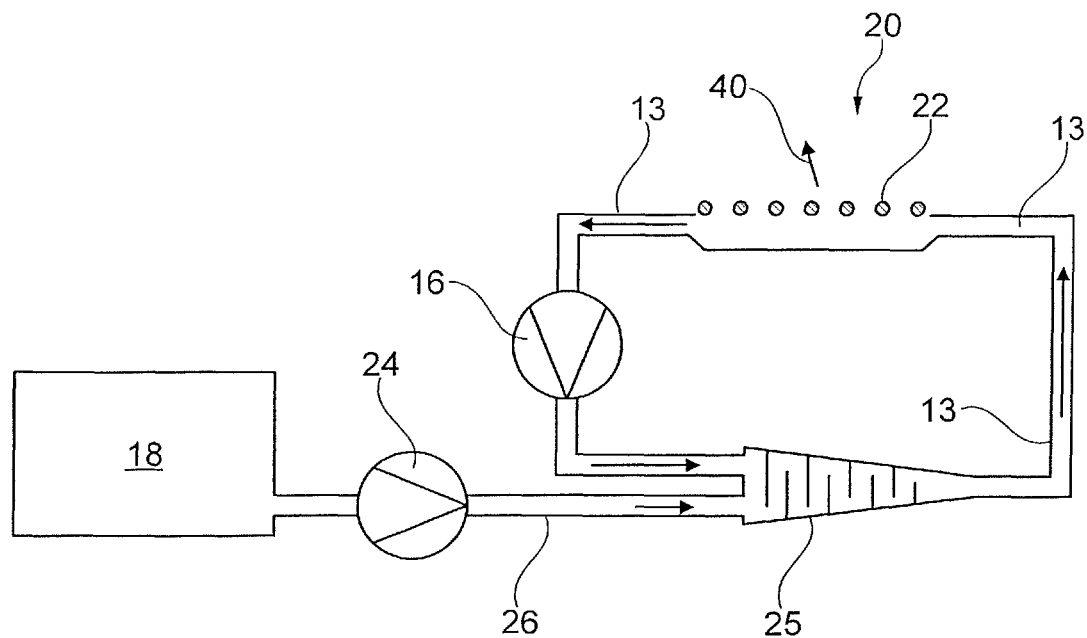
Figure 7:
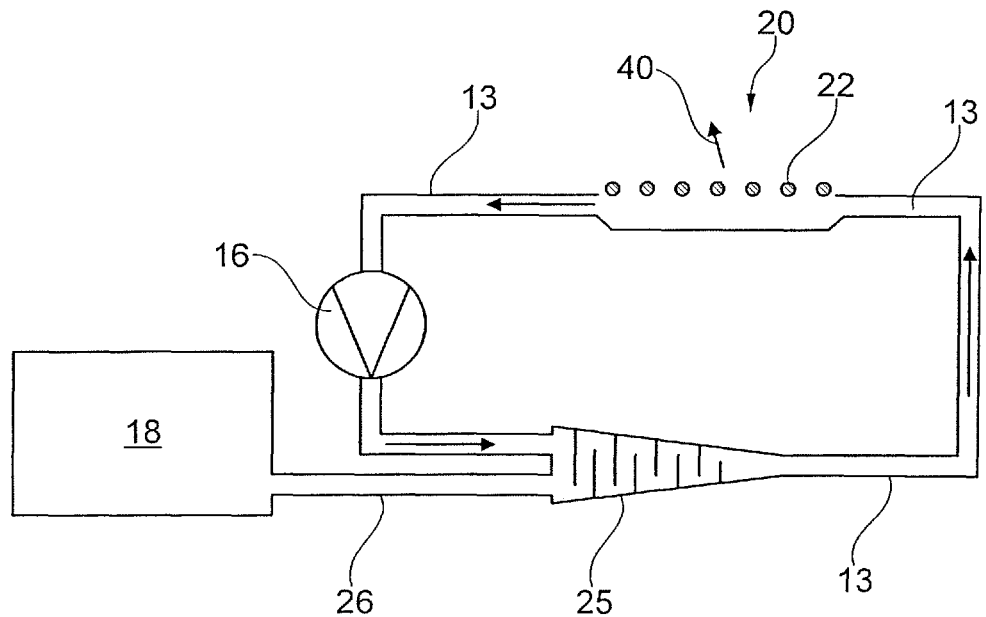

In the embodiment according to FIGS. 6 and 7, the liquid storage 18 is not switched into the circulation line 13 but arranged separated. Liquid is fed from the liquid storage 18 into the circulation line 13 via a branching element 25. The branching element 25 has three ports, namely two ports for inlet to and outlet from the circulation line 13 and one further inlet which is connected to the liquid storage 18 via a separate line 26. The branching element 25 is preferably realized as a mixer, preferred as a static mixer, for example as a labyrinth mixer.

In a not-shown embodiment, mixer 25 and evaporator 20 or heating element 22 may be combined in a single mixer-evaporator-element.

Feeding of liquid from the liquid storage 18 can be realized by a further micropump 24, as can be seen in FIG. 6. The vaporized liquid is fed from the tank 18 by the second micropump 24 and is mixed in the static mixer 25 with the circulating mass flow in the circulation line 13 resulting in a preferably homogeneous liquid mixture.

The feed pump 24 can be omitted, see FIG. 7, if an automatic feeding is realized, for example by capillary effect, pressurizing or by another way.

Additionally or alternatively to the feeding by capillary effect or feed pump 24, other feeding mechanisms may be provided. For example in the embodiments according to FIGS. 3 and 7, pressurizing the liquid storage 18 may be realized. In any case, feeding of the individual vaporized liquid volume is essential, maintaining the forced convection in the circulation line 13, if necessary.

The evaporator unit 17, comprising evaporator 20, pump 16, optionally mixer and connecting lines, is preferably realized as small as possible in order to avoid high thermal loads and corresponding poor responsiveness. The evaporator 20 and/or the evaporator unit are preferably produced on the base of MEMS technology and thus as a microelectromechanical system.

The control arrangement 29 is adjusted in a way that a preferred amount of liquid in the range between 1 µl and 20 µl, more preferred between 2 µl and 10 µl, even more preferred between 3 µl and 5 µl, typically 4 µl per puff of the consumer, is dispensed. The liquid volume per puff is preferably adjustable.

The dispenser/evaporator combination may be preferably adjusted in a way that predominantly liquid drops with a diameter in the range between 0.05 µm and 5 µm, preferred between 0.1 µm and 3 µm are created. Droplet sizes in the range between 0.05 and 5 MMAD (mass median aerodynamic diameter), preferred between 0.1 and 3 MMAD, more preferred between 0.5 and 2 MMAD, even more preferred between 0.7 and 1.5 MMAD, for example about 1 MMAD may be optimal. MMAD corresponds to a EU standard and is specified in µm.

Control of the circulation device 16 is realized by the electronic control arrangement 29. To reduce the power consumption of the circulation device 16, it may be advantageous if the circulation device 16 is not running permanently but phased, because after a certain period of usage of the circulation device 16 a substantially complete mixing of the liquid is provided and further circulation has no significant further advantage. For example, the circulation device 16 may be switched on when a puff by the consumer is determined. The circulation device 16 then may be switched off with or after the completion of the consumer's puff. This may happen immediately or within a predetermined time delay. For example, the circulation device 16 may be switched off, if after a predetermined time period, which for example may range between 3 s and 60 s, no further puff by the consumer is determined. If the inhaler 10 comprises an on-/off-switch, the circulation device 16 may be activated with switching on the inhaler 10, may be operated for at least a predetermined time period and may be switched off if no further puff by the consumer is determined during that time period. Furthermore, when the inhaler 10 is switched off, the circulation device 16 may be deactivated immediately or after a predetermined time delay.

The invention claimed is:

1. An evaporator unit for an inhaler, comprising:
an evaporator,
wherein the evaporator comprises:
a heating element;
a circulation line in which the evaporator is arranged;
a circulation device arranged in the circulation line,
wherein the circulation device circulates a liquid through the circulation line so as to feed the liquid through the evaporator,
wherein the heating element vaporizes at least a portion of the liquid fed through the evaporator;
a liquid storage,
wherein the liquid is stored in the liquid storage; and
a branching element,
wherein the liquid stored in the liquid storage is fed into the circulation line via the branching element, and
wherein the branching element is a mixer.

2. The evaporator unit according to claim 1,
wherein the circulation device is driven electrically.

3. The evaporator unit according to claim 1,
wherein the circulation device is a pump.

4. The evaporator unit according to claim 1,
wherein the circulation device is a micropump.

5. The evaporator unit according to claim 1,
wherein a capillary feed, a feed pump, or a pressurizing device is provided for feeding vaporized liquid.

6. The evaporator unit according to claim 1,
wherein the liquid storage is arranged in the circulation line.

7. The evaporator unit according to claim 1,
wherein the branching element is a static mixer.

8. The evaporator unit according to claim 1,
wherein the evaporator unit is a single microelectromechanical system.

9. An inhaler, comprising:
an evaporator unit according to claim 1.

10. The inhaler according to claim 9,
wherein the circulation device is driven electrically.

11. The inhaler according to claim 9,
wherein the circulation device is a pump.
12. The inhaler according to claim 9,
wherein the circulation device is a micropump.
13. The inhaler according to claim 9,
wherein a capillary feed, a feed pump, or a pressurizing device is provided for feeding vaporized liquid.
14. The inhaler according to claim 9,
wherein the liquid storage is arranged in the circulation line.
15. The inhaler according to claim 9,
wherein the branching element is a static mixer.
16. The inhaler according to claim 9,
wherein the evaporator unit is a single microelectromechanical system.

* * * * *